(12) United States Patent
Yokhin et al.

(10) Patent No.: US 7,680,243 B2
(45) Date of Patent: Mar. 16, 2010

(54) X-RAY MEASUREMENT OF PROPERTIES OF NANO-PARTICLES

(75) Inventors: Boris Yokhin, Nazareth Illit (IL); Alexander Tokar, Haifa (IL); Alexander Krokhmal, Haifa (IL); Asher Peled, Even Yehuda (IL); Dileep Agnihotri, Round Rock, TX (US)

(73) Assignee: Jordan Valley Semiconductors Ltd., Migdal Ha'emek (IL)

( * ) Notice: Subject to any disclaimer, the term of this patent is extended or adjusted under 35 U.S.C. 154(b) by 124 days.

(21) Appl. No.: 11/896,909

(22) Filed: Sep. 6, 2007

(65) Prior Publication Data

US 2009/0067573 A1 Mar. 12, 2009

(51) Int. Cl.
*G01N 23/223* (2006.01)
*G01N 23/201* (2006.01)

(52) U.S. Cl. .......................................... 378/45; 378/88
(58) Field of Classification Search ............. 378/40–44, 378/86–90
See application file for complete search history.

(56) References Cited

U.S. PATENT DOCUMENTS

| | | |
|---|---|---|
| 3,980,568 A | 9/1976 | Pitchford et al. |
| 4,446,568 A | 5/1984 | Williams et al. |
| 4,725,963 A | 2/1988 | Taylor et al. |
| 4,847,882 A | 7/1989 | Knoth et al. |
| 4,916,720 A | 4/1990 | Yamamoto et al. |
| 4,989,226 A | 1/1991 | Woodbury et al. |
| 5,151,588 A | 9/1992 | Kiri et al. |
| 5,481,109 A | 1/1996 | Ninomiya et al. |
| 5,574,284 A | 11/1996 | Farr |
| 5,619,548 A | 4/1997 | Koppel |
| 5,740,226 A | 4/1998 | Komiya et al. |
| 5,900,645 A | 5/1999 | Yamada |
| 5,923,720 A | 7/1999 | Barton et al. |
| 5,937,026 A | 8/1999 | Satoh |
| 5,949,847 A * | 9/1999 | Terada et al. .................. 378/90 |
| 5,963,329 A | 10/1999 | Conrad et al. |
| 6,041,095 A | 3/2000 | Yokhin |
| 6,041,098 A | 3/2000 | Touryanski et al. |

(Continued)

FOREIGN PATENT DOCUMENTS

JP 6160312 A 6/1994

(Continued)

OTHER PUBLICATIONS

Bowen et al., "X-Ray Metrology by Diffraction and Reflectivity", 2000 International Conference on Characterization and Metrology for ULSI Technology, NIST, Gaithersburg, Maryland, USA, Jun. 26-29, 2000.

(Continued)

*Primary Examiner*—Hoon Song
(74) *Attorney, Agent, or Firm*—Smith, Gambrell & Russell, LLP

(57) ABSTRACT

A method for analyzing a sample includes directing one or more beams of X-rays to impinge on an area of a surface of the sample on which a layer of nano-particles of a selected element has been formed. Secondary X-ray radiation from the area is detected responsively to the one or more beams. A distribution of the nano-particles on the surface is characterized based on the detected radiation.

16 Claims, 2 Drawing Sheets

U.S. PATENT DOCUMENTS

| | | | |
|---|---|---|---|
| 6,108,398 | A | 8/2000 | Mazor et al. |
| 6,192,103 | B1 | 2/2001 | Wormington et al. |
| 6,226,347 | B1 | 5/2001 | Golenhofen |
| 6,226,349 | B1 | 5/2001 | Schuster et al. |
| 6,351,516 | B1 | 2/2002 | Mazor et al. |
| 6,381,303 | B1 * | 4/2002 | Vu et al. ............... 378/46 |
| 6,389,102 | B2 | 5/2002 | Mazor et al. |
| 6,453,002 | B1 | 9/2002 | Mazor et al. |
| 6,453,006 | B1 | 9/2002 | Koppel et al. |
| 6,507,634 | B1 | 1/2003 | Koppel et al. |
| 6,512,814 | B2 | 1/2003 | Yokhin et al. |
| 6,556,652 | B1 | 4/2003 | Mazor et al. |
| 6,639,968 | B2 | 10/2003 | Yokhin et al. |
| 6,643,354 | B2 | 11/2003 | Koppel et al. |
| 6,680,996 | B2 | 1/2004 | Yokhin et al. |
| 6,704,661 | B1 | 3/2004 | Opsal et al. |
| 6,711,232 | B1 | 3/2004 | Janik |
| 6,744,850 | B2 | 6/2004 | Fanton et al. |
| 6,744,950 | B2 | 6/2004 | Aleksoff |
| 6,750,952 | B2 | 6/2004 | Grodnensky et al. |
| 6,754,304 | B1 | 6/2004 | Kumakhov |
| 6,754,305 | B1 | 6/2004 | Rosencwaig et al. |
| 6,771,735 | B2 | 8/2004 | Janik et al. |
| 6,810,105 | B2 | 10/2004 | Nasser-Ghodsi et al. |
| 6,823,043 | B2 | 11/2004 | Fewster et al. |
| 6,895,075 | B2 | 5/2005 | Yokhin et al. |
| 6,947,520 | B2 | 9/2005 | Yokhin et al. |
| 6,977,986 | B1 | 12/2005 | Beanland et al. |
| 7,023,954 | B2 | 4/2006 | Rafaeli et al. |
| 7,062,013 | B2 | 6/2006 | Berman et al. |
| 7,068,753 | B2 | 6/2006 | Berman et al. |
| 7,071,007 | B2 | 7/2006 | Tseng et al. |
| 7,103,142 | B2 | 9/2006 | Agnihotri et al. |
| 7,110,491 | B2 | 9/2006 | Mazor et al. |
| 7,120,228 | B2 | 10/2006 | Yokhin et al. |
| 7,130,376 | B2 | 10/2006 | Berman et al. |
| 7,245,695 | B2 | 7/2007 | Mazor et al. |
| 2001/0028699 | A1 | 10/2001 | Iwasaki |
| 2001/0043668 | A1 | 11/2001 | Hayashi et al. |
| 2002/0097837 | A1 | 7/2002 | Fanton et al. |
| 2002/0110218 | A1 | 8/2002 | Koppel et al. |
| 2002/0150208 | A1 | 10/2002 | Yokhin et al. |
| 2003/0012337 | A1 | 1/2003 | Fewster et al. |
| 2003/0128809 | A1 | 7/2003 | Umezawa et al. |
| 2003/0157559 | A1 | 8/2003 | Omote et al. |
| 2004/0052330 | A1 | 3/2004 | Koppel et al. |
| 2004/0109531 | A1 | 6/2004 | Yokhin et al. |
| 2004/0131151 | A1 | 7/2004 | Berman et al. |
| 2004/0156474 | A1 | 8/2004 | Yokhin et al. |
| 2004/0218717 | A1 | 11/2004 | Koppel et al. |
| 2004/0267490 | A1 | 12/2004 | Opsal et al. |
| 2005/0195940 | A1 * | 9/2005 | Ito ............... 378/58 |
| 2005/0211910 | A1 * | 9/2005 | Bloom et al. ............. 250/423 P |
| 2006/0062351 | A1 | 3/2006 | Yokhin et al. |

FOREIGN PATENT DOCUMENTS

| | | |
|---|---|---|
| JP | 7092112 A | 4/1995 |
| JP | 7098285 A | 4/1995 |
| JP | 2002310947 A | 10/2002 |
| WO | 01/24200 A2 | 4/2001 |

OTHER PUBLICATIONS

Dane et al., "Application of Genetic Algorithms for Characterization of Thin Layered Materials by Glancing Incidence X-Ray Reflectometry", Physica B 253, pp. 254-268, 1998 Elsevier Science B.V.

Huang et al., "Characterization of Single- and Multiple-Layer Films by X-Ray Reflectometry", Advances in X-Ray Analysis, vol. 35, pp. 137-142, Plenum Press, New York, USA, 1992.

Kozaczek et al., "X-Ray Diffraction Metrology for 200 MM Process Qualification and Stability Assessment", Advanced Metallization Conference, Montreal, Canada, Oct. 8-11, 2001.

Lankosz et al., "Research in Quantitative X-Ray Fluorescence Microanalysis of Patterned Thin Films", Advances in X-Ray Analysis, vol. 43, pp. 497-503, 48th Annual Denver X-Ray Conference, Steamboat Springs, Colorado, USA, Aug. 2-6, 1999.

Leng et al., "Simultaneous Measurement of Six Layers in a Silicon on Insulator Film Stack Using Spectrophotometry and Beam Profile Reflectometry", Journal of Applied Physics, vol. 81(8), American Institute of Physics, Apr. 15, 1997.

Lengeler, Bruno, "X-Ray Reflection, a New Tool for Investigating Layered Structures and Interfaces", Advances in X-Ray Analysis, vol. 35, pp. 127-135, Plenum Press, New York, USA, 1992.

Levine Parrill et al., "GISAXS—Glancing Incidence Small Angles X-Ray Scattering", Journal de Physique IV, supplement to Journal de Physique I, vol. 3, pp. 411-417, Dec. 1993.

Naudon et al., "New Apparatus for Grazing X-Ray Reflectometry in the Angle-Resolved Dispersive Mode", Journal of Applied Crystallography, vol. 22, pp. 460-464, International Union of Crystallography, 1989.

Neissendorfer et al., "The Energy-Dispersive Reflectometer/Diffractometer at BESSY-I", Measurement Science and Technology Journal, edition 10, pp. 354-361, IOP Publishing Ltd., UK, 1999.

Powell et al., "X-Ray Diffraction and Reflectivity Characterization of SiGe Superlattice Structures", Semiconductor Science and Technology, edition 7, pp. 627-631, IOP Publishing Ltd., UK, 1992.

Ulyanenkov, Alex, "Introduction to High Resolution X-Ray Diffraction", Workshop on X-Ray Characterization of Thin Layers, Uckley, May 21-23, 2003.

U.S. Appl. No. 60/753,895 "Accurate Measurement of Layer Dimensions Using XRF" filed on Dec. 22, 2005.

U.S. Appl. No. 60/800,589 "Automated Selection of X-Ray Reflectometry Measurement Locations" filed on May 15, 2006.

English Abstract of Japanese Publication "X-Ray Diffraction Device", published on Feb. 20, 1998, under publication No. JP10048398A.

English Abstract of Japanese Patent Application "Inspection Device and Semiconductor Inspection Method", published on Dec. 4, 1998, under the publication No. JP10318949A.

* cited by examiner

X-RAY MEASUREMENT OF PROPERTIES OF NANO-PARTICLES

FIELD OF THE INVENTION

The present invention relates generally to non-destructive testing, and specifically to instruments and method for material analysis using X-rays.

BACKGROUND OF THE INVENTION

X-ray fluorescence (XRF) measurement, and specifically X-ray microfluorescence (i.e., X-ray fluorescence using narrow, focused excitation beams), is gaining increasing attention as a method for testing semiconductor wafers. XRF itself is a well-known technique for determining the elemental composition of a sample. XRF analyzers generally include an X-ray source, which irradiates the sample, and an X-ray detector, for detecting the X-ray fluorescence emitted by the sample in response to the irradiation. Each element in the sample emits X-ray fluorescence in energy bands that are characteristic of the element. The detected X-ray fluorescence is analyzed to find the energies or, equivalently, the wavelengths of the detected photons, and the qualitative and/or quantitative composition of the sample is determined based on this analysis.

U.S. Pat. No. 6,108,398, for example, whose disclosure is incorporated herein by reference, describes an XRF analyzer and a method for analyzing a sample. The analyzer includes an X-ray beam generator, which generates an X-ray beam incident at a spot on the sample and creates a plurality of fluorescent X-ray photons. An array of semiconductor detectors is arranged around the spot so as to capture the fluorescent X-ray photons. The analyzer produces electrical pulses suitable for analysis of the sample.

Small-angle X-ray scattering (SAXS) is another X-ray based method, which may be used for surface layer characterization. It is described, for example, by Parrill et al., in "GISAXS—Glancing Incidence Small Angle X-ray Scattering," *Journal de Physique IV* 3 (December, 1993), pages 411-417, which is incorporated herein by reference. In this method, an incident X-ray beam is totally externally reflected from a surface. The evanescent wave within the surface region is scattered by microscopic structures within the region. Measurement of the scattered evanescent wave can provide information about these structures. For example, Parrill et al. describe the use of this technique for determining size information regarding islands associated with film growth on the surface.

SAXS may be combined with X-ray reflectometry (XRR) measurements, as described, for example, in U.S. Pat. No. 6,895,075, whose disclosure is incorporated herein by reference. In the embodiments disclosed in this patent, X-ray inspection apparatus comprises a radiation source, which is configured to irradiate a small area on a surface of a sample. The X-ray optics control the radiation beam so as to adjust the angular width and height of the beam appropriately for XRR or SAXS. An array of detector elements is positioned to detect radiation that is scattered from the irradiated area as a function of azimuth for SAXS or of elevation angle for XRR.

Techniques have been developed recently for depositing nano-particles on a substrate. In the context of the present patent application and in the claims, the term "nano-particle" refers to particles whose dimensions are normally measured in nanometers, i.e., particles having a dimension between 1 nm and 999 nm. For example, U.S. Pat. No. 7,071,007 describes a method of forming a low-voltage drive thin film ferroelectric capacitor, which includes a nanocomposite layer including nano-particles of platinum. The nanocomposite structure and particle sizes are observed using a transmission electron microscope (TEM).

SUMMARY OF THE INVENTION

Embodiments of the present invention that are described hereinbelow provide improved methods and systems for characterizing a layer of nano-particles that is formed on a substrate, based on secondary X-ray radiation from the layer. In some of these methods, small-angle X-ray scattering (SAXS, as defined above) is used to determine size characteristics of the nano-particles. The intensity of emission in X-ray fluorescence (XRF) lines of an element comprised in the nano-particles is measured in order to determine the quantity of the element in the layer. The particle size and element quantity characteristics are combined in order to define characteristics of the distribution of the nano-particles in the layer. In this manner, it is possible, for example, to monitor a process of nano-particle deposition so that the layer has the desired distribution of nano-particles in terms of size and packing density.

There is therefore provided, in accordance with an embodiment of the present invention, a method for analyzing a sample, including:

directing one or more beams of X-rays to impinge on an area of a surface of the sample on which a layer of nano-particles of a selected element has been formed;

detecting secondary X-ray radiation from the area responsively to the one or more beams; and characterizing a distribution of the nano-particles on the surface based on the detected radiation.

Typically, the one or more beams include a beam that is incident on the surface at a grazing angle, and detecting the secondary X-ray radiation includes detecting an angular spectrum of the X-rays that are scattered from the area responsively to the beam that is incident at the grazing angle. In some embodiments, detecting the angular spectrum includes resolving the scattered X-rays as a function of scattering angle in a plane of the surface, and characterizing the distribution includes processing the angular spectrum as a function of the scattering angle in order to determine a characteristic size of the particles. Processing the angular spectrum may include computing a parametric fit to a scattering function so as to determine a mean and a variance of a characteristic dimension of the particles.

In some embodiments, detecting the secondary X-ray radiation includes detecting an intensity of X-ray fluorescence emitted from the sample in a spectral line that is characteristic of the selected element responsively to at least one of the one or more beams. Typically, the one or more beams include a beam that is incident on the surface at a grazing angle, and wherein detecting the secondary X-ray radiation detecting an angular spectrum of the X-rays that are scattered from the area responsively to the beam that is incident at the grazing angle, and characterizing the distribution includes deriving one or more characteristics of the nano-particles from the intensity of the X-ray fluorescence and the angular spectrum of the scattered X-rays.

In a disclosed embodiment, deriving the one or more characteristics includes finding a quantity of the selected element that is present in the area responsively to the intensity of the X-ray fluorescence emitted in the spectral line, and finding a characteristic size of the nano-particles responsively to the angular spectrum of the scattered X-rays. Typically, determining the one or more characteristics includes computing, based on the quantity of the selected element and the characteristic size of the nano-particles, a feature of the layer of the nano-particles selected from a group of features consisting of a numerical density and a fill factor of the nano-particles.

In an alternative embodiment, detecting the secondary X-ray radiation includes detecting the X-rays that are reflected from the surface as a function of elevation angle relative to a plane of the surface.

The method may include controlling a process of deposition of the nano-particles on the surface responsively to a characteristic of the distribution.

There is also provided, in accordance with an embodiment of the present invention, apparatus for analyzing a sample, including:

at least one radiation source, which is configured to direct one or more beams of X-rays to impinge on an area of a surface of the sample on which a layer of nano-particles of a selected element has been formed;

at least one detector, which is configured to receive secondary X-ray radiation from the area responsively to the one or more beams and to generate signals responsively to the received radiation; and a signal processor, which is coupled to receive and process the signals so as to characterize a distribution of the nano-particles on the surface.

The present invention will be more fully understood from the following detailed description of the embodiments thereof, taken together with the drawings in which:

DETAILED DESCRIPTION OF EMBODIMENTS

Figure 1:
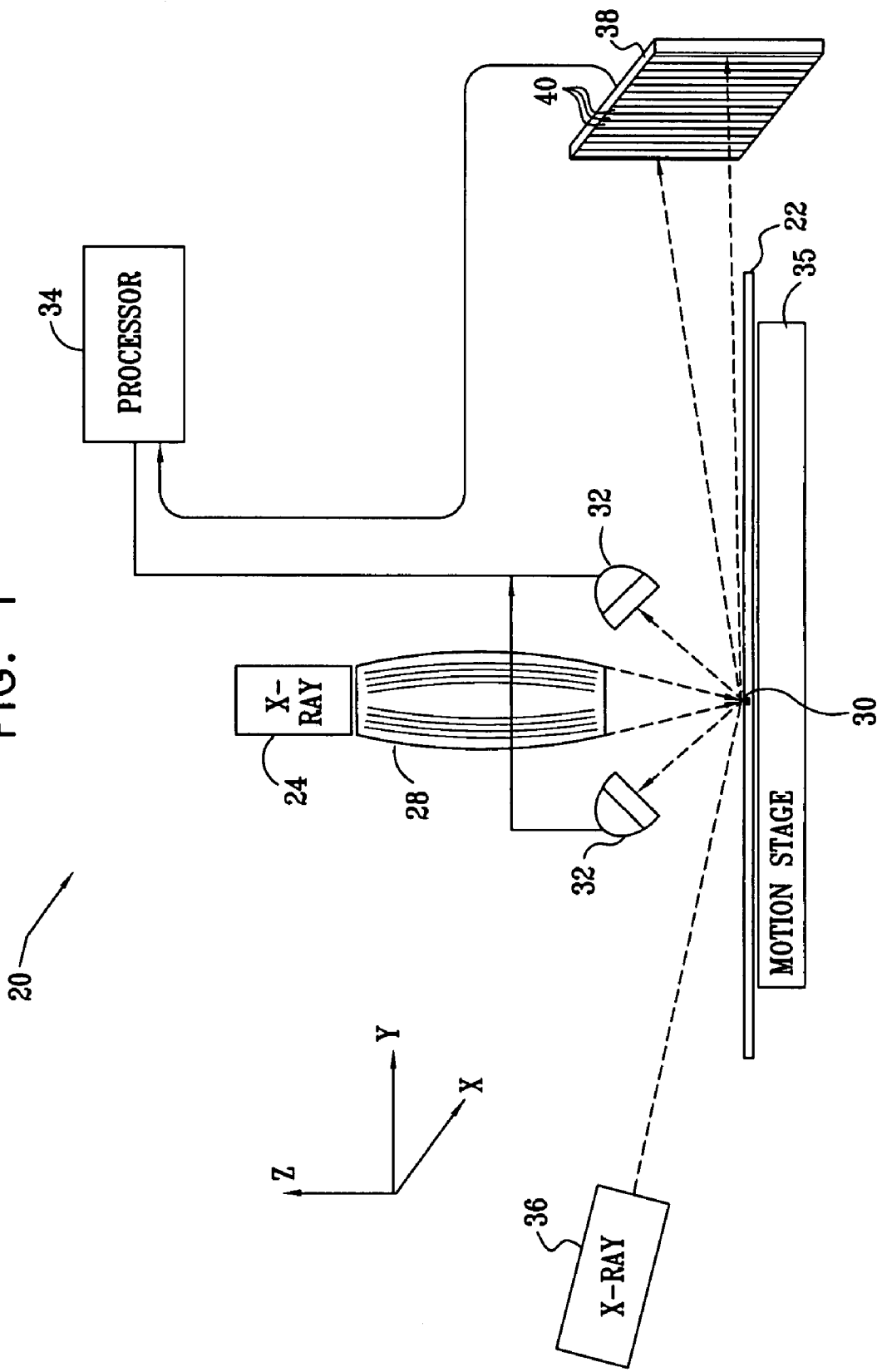
FIG. 1 is a schematic side view of a system for measuring properties of a nano-particle layer, in accordance with an embodiment of the present invention.

FIG. 1 is a schematic side view of a system 20 for measuring properties of a nano-particle layer on a sample 22, in accordance with an embodiment of the present invention. Sample 22 may be, for example, a semiconductor wafer, but the principles of this embodiment are similarly applicable to layers of nano-particles that are formed on substrates of other sorts. System 20 operates by irradiating sample 22 with X-rays, detecting secondary X-ray radiation that is emitted from the sample in response to the irradiation, and analyzing the detected radiation in order to determine characteristics of the nano-particles on the sample. In the context of the present patent application and in the claims, the term "secondary radiation" refers to any and all processes by which X-ray irradiation of a sample causes X-rays to be emitted from the sample. Thus, in this context, "secondary radiation" includes the phenomena of XRF and SAXS, as well as other scattering phenomena known in the art, such as XRR and X-ray diffraction (XRD).

System 20 performs the functions of an XRF analyzer and a SAXS spectrometer. The XRF analyzer function measures X-ray fluorescence emitted from a small area 30 on the surface of sample 22. Area 30 is typically no greater than 100 µm across, and may be smaller than 20 µm, although the principles of the present invention may similarly be applied to larger areas. Aspects of this sort of X-ray microfluorescence analysis are described in detail in the above-mentioned U.S. Pat. No. 6,108,398. The SAXS spectrometry function measures small-angle scattering from area 30 in a manner similar to that described in the above-mentioned U.S. Pat. No. 6,895,075. The XRF and SAXS functions are shown in FIG. 1 as taking place with sample 22 in a single location using an integrated system, but the XRF and SAXS measurements may alternatively take place in different locations, using different measurement systems, which are mutually registered so that the XRF and SAXS measurements may be applied to the same area of the sample.

For the purpose of the XRF measurement, system 20 comprises an excitation source 24, such as an X-ray tube, which emits a beam of X-rays having a suitable energy range and power flux into X-ray optics 28. For example, for XRF analysis of nano-particles containing platinum, an X-ray tube with a molybdenum anode may be operated at a voltage of about 45 kV, in order to excite the Pt L$\alpha$ emission line. Alternatively, other tube configurations and voltages may be used, depending, inter alia, on the elemental composition of the nano-particles in question. The optics may comprise a polycapillary array, for example. Optics 28 focus the X-ray beam onto area 30. Although source 24 is positioned in FIG. 1 perpendicularly above sample 22, the source may alternatively be positioned so that the X-ray beam impinges on the surface of the sample at an angle. In response to the incident beam, area 30 emits fluorescent X-rays, which are captured by one or more detectors 32. These detectors may be arranged around region 30 and angled toward it, as shown in FIG. 1. Responsively to the captured photons, detectors 32 generate electrical signals, which are conveyed to a signal processor 34.

Processor 34 typically comprises an energy-dispersive pulse processing system, as is known in the art, which determines an intensity spectrum of the X-ray photons captured by the detectors. Alternatively, a wavelength-dispersive detection and processing system may be used. Each chemical element within the irradiated region that is excited by the X-rays from tube 24 emits fluorescent X-rays in characteristic spectral lines. The intensity of the characteristic spectral lines of a given element is proportional to the mass of that element within area 30. Thus, processor 34 uses the determined intensity spectra to determine how much of a particular material is present within the region of area 30.

For the purposes of spectral analysis, processor 34 typically comprises a general-purpose computer, which performs these functions under the control of suitable software. The software may be downloaded to the processor in electronic form, over a network, for example, or it may alternatively be provided on tangible media, such as optical, magnetic or electronic memory media.

In order to perform the SAXS measurement, an X-ray source 36 emits a narrow, monochromatic X-ray beam that is approximately collimated and strikes area 30 at a grazing angle, i.e., at a small angle relative to the surface of sample 22, which is generally at the critical angle for total external reflection or slightly above or below this angle. Source 36 typically comprises an X-ray tube with suitable monochromatizing and collimating optics (not shown in the figures), such as the optical arrangement described in the above-mentioned U.S. Pat. No. 6,895,075. The X-ray tube used in source 36 may be the same one that is used for the XRF measurements, or it may be a different tube, with a different type of anode and operating voltage, such as the types and voltages described in U.S. Pat. No. 6,895,075. When the same tube is used for both XRF and XRR, the tube (and possibly the X-ray optics, as well)

may be movable between the positions of source 24 and source 36 that are shown in FIG. 1, for example.

Alternatively, for some types of samples, XRF may be measured using an excitation beam at grazing incidence, i.e., with the source in the position of source 36. Analysis of the fluorescence emitted when the sample is excited at an angle below the critical angle for total external reflection of the incident X-rays is known in the art as total reflection X-ray fluorescence (TXRF) analysis. Details of this technique are described, for example, by Lengeler, in "X-ray Reflection, a New Tool for Investigating Layered Structures and Interfaces," *Advances in X-ray Analysis* 35 (1992), p. 127, which is incorporated herein by reference.

X-rays scattered from area 30 due to irradiation by source 36 are detected by a detector array 38, such as a CCD array, comprising multiple detector elements 40, as described in the above-mentioned U.S. Pat. No. 6,895,075, for example. Although for simplicity of illustration, only a single row of detectors elements is shown in the figures, with a relatively small number of detector elements, array 38 generally includes a greater number of elements, arranged as either a linear array or a matrix (two-dimensional) array. When a linear array is used, the axis of array 38 may be oriented in the X-direction, parallel to the plane of sample 22. Thus, elements 40 resolve the scattered X-rays along the X-axis, i.e., as a function of azimuth in the sample plane. Alternatively, using a matrix array, the two-dimensional axially-symmetric scattering pattern may be measured as a function of radial angle in the X-Z plane. Optionally, detector array 38 may also be used for XRF measurements, in place of or in addition to the separate detectors 32.

Sample 22 is typically mounted on a motion stage 35, which permits the position and orientation of the sample to be adjusted relative to the X-ray sources and detectors. Stage 35 may be operated to scan the X-ray beams over different areas of the sample. Alternatively, the sample may be mounted on a suitable stationary fixture while the X-ray sources and detectors are moved.

Processor 34 analyzes the output of array 38, so as to determine a distribution of the flux of X-ray photons scattered from sample 22 as a function of angle at a given energy or over a range of energies. The distribution of the scattered X-rays as a function of angle is indicative of microstructure, such as nano-particles, in the surface layer of sample 22. Processor 34 analyzes characteristics of the angular distribution in order to determine characteristics of the nano-particles, particularly the sizes of the particles, using methods of analysis described hereinbelow.

Although certain particular configurations of the excitation sources and X-ray detectors in system 20 are shown in FIG. 1 and described hereinabove by way of illustration, other types of fluorescence and scattering analyzers known in the art, comprising any suitable excitation source, optics and detection system, may alternatively be used for implementing the methods described herein.

Optionally, source 36 and array 38 may be configured to perform X-ray reflectometry (XRR) measurements, in addition to or instead of the above-mentioned SAXS measurements. For this purpose, source 36 may be configured so that the beam it emits converges onto area 30 over a range of elevation angles, and array 38 may be rotated or otherwise configured to resolve the radiation that is reflected from area 30 along the Z-axis, i.e., as a function of elevation relative to the sample plane. This sort of dual-function XRR/SAXS operation is described in the above-mentioned U.S. Pat. No. 6,895,075. Additionally or alternatively, analyzer 20 may be further configured to capture and process secondary X-ray radiation from wafer 22 due to other mechanisms, such as diffraction. Multi-function systems of this sort are described, for example, the above-mentioned U.S. Pat. No. 6,895,075, as well as in U.S. Pat. No. 6,381,303 and in U.S. Patent Application Publication 2006/0062351, whose disclosures are incorporated herein by reference.

Figure 2:
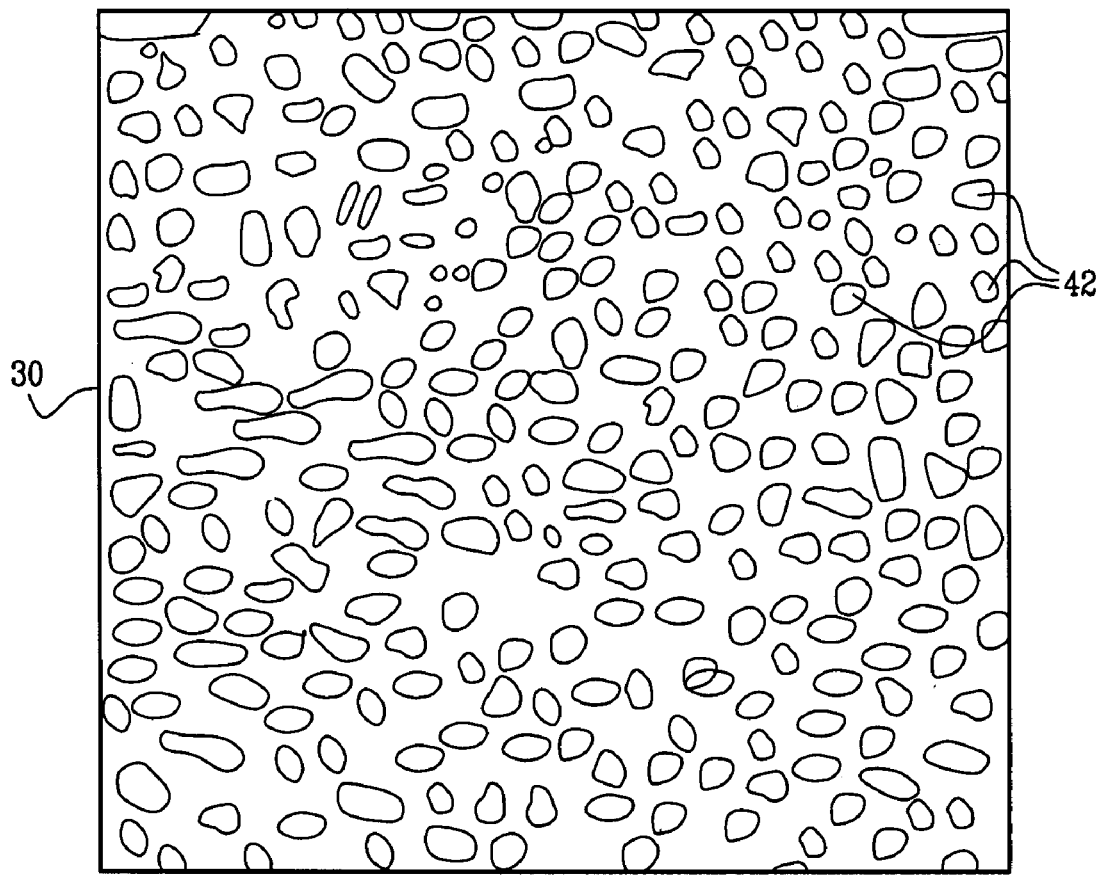
FIG. 2 is a schematic, top view of a layer of nano-particles, whose characteristics are measured in accordance with an embodiment of the present invention.

FIG. 2 is a schematic top view of area 30, showing a typical layer of nano-particles 42 that is formed in the area. The nano-particles comprise one or more predetermined elements, such as platinum, as in the above-mentioned U.S. Pat. No. 7,071,007. The distribution of the nano-particles in area 30 can be characterized in terms of the sizes of the particles and the number of particles per unit area, i.e., how densely the particles are packed together in the layer. In a semiconductor device containing nano-particles, the sizes and number of nano-particles per unit area affect the electrical properties and performance of the device. It is therefore important to the manufacturer to know and to be able to control these parameters.

The particle size distribution can be expressed in terms of a mean particle diameter and a variance about the mean. These size parameters can be inferred from the SAXS angular spectrum received from detector array 38, as described hereinbelow. The intensity of the scattered radiation in the SAXS spectrum is roughly indicative of the number of particles per unit area, but does not by itself give an accurate reading of this parameter. It is therefore advantageous to measure the intensity of one or more XRF emission lines of the element (or elements) from which the nano-particles are made. This intensity is proportional to the quantity of the element that is present in area 30, and thus, for a known particle size, to the number of particles per unit area.

Figure 3:
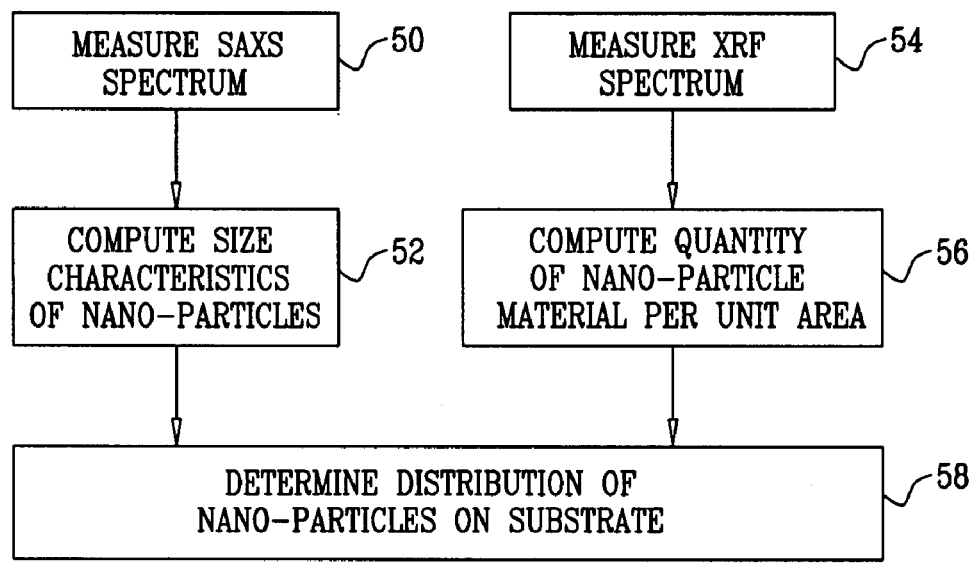
FIG. 3 is a flow chart that schematically illustrates a method for characterizing a nano-particle layer, in accordance with an embodiment of the present invention.

FIG. 3 is a flow chart that schematically illustrates a method for characterizing a layer of nano-particles 42 formed in area 30 of sample 22, in accordance with an embodiment of the present invention. The method is described, for the sake of clarity, with reference to system 20, but the principles of this method may similarly be implemented using other means of SAXS and XRF measurement.

System 20 is operated to measure the SAXS angular spectrum of area 30, at a SAXS measurement step 50. For this purpose, X-ray source 36 irradiates area 30, and detector array 38 measures the intensity of scattered X-rays that is received by each detector element 40. Processor 34 analyzes the SAXS spectrum in order to determine the size characteristics of nano-particles 42, at a size computation step 52. As noted above, the size characteristics can be expressed in terms of a mean particle diameter and a variance of the diameters. A theoretical SAXS spectrum may be computed as a function of the diameter and variance parameters. To determine the size characteristics, processor 34 may find the parameter values that give the best fit between the theoretical spectrum and the actual measured spectrum.

Substantially any method of fitting known in the art may be used at step 52. The purpose of the fit is to find values of the mean diameter $R_0$ and the variance $\sigma$, along with an amplitude constant C, that optimally match the distribution of scattered intensity $I(Q)$. (For convenience, the fit may be computed in terms of the momentum transfer parameter $Q = 4\pi \sin\theta/\lambda$, as is common in the art of X-ray scattering measurement, wherein $2\theta$ is the scattering angle, and $\lambda$ is the X-ray wavelength.) The fit may be performed using the expression:

$$I(Q) = C \int_{R\min}^{R\max} dR \cdot [F^2(Q, R)] \cdot n(R) \quad (1)$$

Here R is the particle size, and $R_{max}$ and $R_{min}$ are heuristic maximum and minimum size limits. F is a scattering form factor given by:

$$F(Q, R) = 3 \cdot V(R) \cdot \frac{\sin(QR) - QR \cdot \cos(QR)}{(QR)^3} \quad (2)$$

assuming spherical particles, wherein V(R) is the volume of a spherical particle of size R. (Alternatively, if the nano-particles have a known non-spherical shape, the scattering form factor may be corrected accordingly.) The distribution of particle sizes n(R) may be approximated as a normal distribution with mean $R_0$ and variance σ, in accordance with the Guinier approximation, or as a log-normal distribution with these parameters. Details of the fitting procedure, as well as alternative methods for processing the scattering results, will be apparent to those skilled in the art.

System 20 is operated to measure the XRF intensity spectrum of area 30, at an XRF measurement step 54. (Although this step and the subsequent computation step are shown and described here as following steps 50 and 52, the order to the steps is arbitrary. The XRF measurement may be performed before the SAXS measurement, and the subsequent computation steps may be performed in any desired order.) At step 54, detectors 32 generate electrical pulses in response to fluorescent X-ray photons that are incident on the detectors, and processor 34 processes the pulse amplitudes in order to determine the energies of the photons. The XRF intensity spectrum is found by counting the number of photons detected at each value of photon energy in the range of interest. As noted above, for a given element in nano-particles 42, the intensity of the corresponding emission lines in the SRF spectrum is proportional to the quantity (i.e., the number of atoms, or the mass) of the element in the area that is irradiated by source 24. Thus, based on the XRF intensity spectrum, processor 34 determines the quantity of the element or elements that make up nano-particles 42 in area 30, at a quantity computation step 56.

Using the results of steps 52 and 56, processor 34 determines the distribution of nano-particles 42 in area 30, at a distribution computation step 58. For this purpose, the processor may use the size parameters found at step 52 and the known specific mass of the element or elements making up the nano-particles to compute an average mass per particle. The processor may use the quantity of the element or elements found at step 56 to compute the average mass of the element or elements per unit area in the nano-particle layer. The quotient of these factors is the numerical density of the particles in area 30 (i.e., the number of particles per unit area). The processor may use the number of particles per unit area together with the average particle size in determining a fill factor, indicating how completely the layer of nano-particles covers the area. The particle size parameters and fill factor may be used in adjusting process parameters so as to achieve the desired packing of nano-particles in the layer. The adjustment may be controlled automatically by processor 34, or by a human operator based on information output by the processor.

Optionally, as noted above, system 20 may be operated to generate an XRR spectrum of area 30, i.e., the distribution of reflected X-rays as a function of elevation angle. The XRR spectrum typically comprises an oscillatory pattern, as described in the above-mentioned U.S. Pat. No. 6,895,075. The period of oscillation is indicative of the thickness of one or more thin film layers on sample 22 (including the layer containing nano-particles 42), while the amplitude of the oscillation is indicative of the roughness of the interfaces between the layers. The angle of total external reflection is given by a "shoulder" in the XRR spectrum, which corresponds to the minimal angle at which the oscillatory pattern begins to appear, and is indicative of the density of the layer. Processor 34 may combine this XRR information with the SAXS and/or XRF information described above in order to extract further characteristics of the nano-particle layer. Alternatively or additionally, system 20 and processor 34 may detect and use other sorts of parameters of secondary X-ray radiation, such as X-ray diffraction parameters.

Although system 20 is shown in the figures, for the sake of simplicity, as operating in a standalone configuration, the functions of this system may alternatively be integrated into the production environment in which the nano-particles are fabricated. For example, system 20 may be configured as a test station in a cluster tool. As another example, the elements of system 20 may be integrated with a material deposition chamber in order to measure the formation of nano-particles in situ during production.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for analyzing a sample, comprising:
    directing one or more beams of X-rays from at least one radiation source to impinge on an area of a surface of the sample on which a layer of nano-particles of a selected element has been formed, including a beam that is incident on the surface at a grazing angle;
    detecting, using at least one detector, an intensity of X-ray fluorescence emitted from the area in a spectral line that is characteristic of the selected element responsively to the one or more beams;
    detecting, using the at least one detector, an angular spectrum of the X-rays that are scattered from the area responsively to the beam that is incident on the surface at the grazing angle; and
    characterizing a distribution of the nano-particles on the surface based on the intensity of the X-ray fluorescence and the angular spectrum of the scattered X-rays.

2. The method according to claim 1, wherein detecting the angular spectrum comprises resolving the scattered X-rays as a function of scattering angle.

3. The method according to claim 2, wherein characterizing the distribution comprises processing the angular spectrum as a function of the scattering angle in order to determine a characteristic size of the particles.

4. The method according to claim 3, wherein processing the angular spectrum comprises computing a parametric fit to a scattering function so as to determine a mean and a variance of a characteristic dimension of the particles.

5. The method according to claim 1, wherein characterizing the distribution comprises finding a quantity of the selected element that is present in the area responsively to the intensity of the X-ray fluorescence emitted in the spectral line, and finding a characteristic size of the nano-particles responsively to the angular spectrum of the scattered X-rays.

6. The method according to claim 5, wherein characterizing the distribution comprises computing, based on the quantity of the selected element and the characteristic size of the nano-particles, a feature of the layer of the nano-particles selected from a group of features consisting of a numerical density and a fill factor of the nano-particles.

7. The method according to claim 1, wherein detecting the secondary X-ray radiation comprises detecting the X-rays that are reflected from the surface as a function of elevation angle relative to a plane of the surface.

8. The method according to claim 1, and comprising controlling a process of deposition of the nano-particles on the surface responsively to a characteristic of the distribution.

9. Apparatus for analyzing a sample, comprising:
   at least one radiation source, which is configured to direct one or more beams of X-rays to impinge on an area of a surface of the sample on which a layer of nano-particles of a selected element has been formed, including a beam that is incident on the surface at a grazing angle;
   at least one detector, which is configured to detect an intensity of X-ray fluorescence emitted from the area in a spectral line that is characteristic of the selected element responsively to the one or more beams and to detect an angular spectrum of the X-rays that are scattered from the area responsively to the beam that is incident on the surface at the grazing angle, and to generate signals responsively to the detected intensity of the X-ray fluorescence and to the angular spectrum; and
   a signal processor, which is coupled to receive and process the signals so as to characterize a distribution of the nano-particles on the surface.

10. The apparatus according to claim 9, wherein the at least one detector is configured to resolve the scattered X-rays as a function of scattering angle.

11. The apparatus according to claim 10, wherein the signal processor is configured to process the angular spectrum as a function of the scattering angle in order to determine a characteristic size of the particles.

12. The apparatus according to claim 11, wherein the signal processor is configured to compute a parametric fit to a scattering function so as to determine a mean and a variance of a characteristic dimension of the particles.

13. The apparatus according to claim 9, wherein the signal processor is configured to find a quantity of the selected element that is present in the area responsively to the intensity of the X-ray fluorescence emitted in the spectral line, and to find a characteristic size of the nano-particles responsively to the angular spectrum of the scattered X-rays.

14. The apparatus according to claim 13, wherein the signal processor is configured to compute, based on the quantity of the selected element and the characteristic size of the nano-particles, a feature of the layer of the nano-particles selected from a group of features consisting of a numerical density and a fill factor of the nano-particles.

15. The apparatus according to claim 9, wherein the at least one detector is configured to detect the X-rays that are reflected from the surface as a function of elevation angle relative to a plane of the surface.

16. The apparatus according to claim 9, wherein the signal processor is configured to control a process of deposition of the nano-particles on the surface responsively to a characteristic of the distribution.

* * * * *